(12) United States Patent
Yoshida

(10) Patent No.: US 7,186,510 B2
(45) Date of Patent: Mar. 6, 2007

(54) METHOD FOR EVALUATING UNIFORMITY OF SPOTS ON AN ARRAY

(75) Inventor: Tetsushiko Yoshida, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 456 days.

(21) Appl. No.: 10/485,030

(22) PCT Filed: Jul. 31, 2002

(86) PCT No.: PCT/JP02/07796

§ 371 (c)(1),
(2), (4) Date: Jan. 29, 2004

(87) PCT Pub. No.: WO03/012411

PCT Pub. Date: Feb. 13, 2003

(65) Prior Publication Data

US 2004/0201840 A1 Oct. 14, 2004

(30) Foreign Application Priority Data

Jul. 31, 2001 (JP) .............................. 2001-232364

(51) Int. Cl.
*C12Q 1/68* (2006.01)
*C12M 1/34* (2006.01)
(52) U.S. Cl. ........................................... 435/6; 702/19
(58) Field of Classification Search .................... 435/6; 702/19, 20
See application file for complete search history.

(56) References Cited

U.S. PATENT DOCUMENTS 6,438,496 B1 * 8/2002 Yoshida et al. ................ 702/19
6,862,532 B2 * 3/2005 Yoshida et al. ................ 702/19
2002/0045181 A1 * 4/2002 Watanabe et al. .............. 435/6

FOREIGN PATENT DOCUMENTS

EP 0 898 236 A2 2/1999

OTHER PUBLICATIONS

Yoshida et al., "Color-coding Reveals Tandem Repeats in the *Escherichia coli* Genome," J. Mol. Biol., 298, No. 3, pp. 343-349, 2000.
Kato, "DNA Microarray," Takara Shuzo Kabushiki Kaisha, pp. 19-45, Sep. 25, 2000.
Matsumura et al., "DNA Microarray to Saishin PCR Ho," Shiujunsha Co., Ltd., pp. 35-54 and 88-89, Mar. 16, 2000.
Yoshida, "Nijigen Shikisai Patern-Ka ni yoru Ichijigen DNA Enki Hairetsu no Joho Kaisekiho," Bioscience & Industry, vol. 60, No. 9, pp. 596-599, Sep. 1, 2002.

* cited by examiner

*Primary Examiner*—Hoa Q. Pham
(74) *Attorney, Agent, or Firm*—Oliff & Berridge, PLC

(57) ABSTRACT

A method for evaluating a uniformity of spots on a DNA microarray having a plurality of spots, these spots undergoing specific emissions as a result of the hybridization of target DNA and tagged probe DNA, by examining whether patterns having periodicity are manifested in a sequence BG comprising background data obtained.

6 Claims, 11 Drawing Sheets
(7 of 11 Drawing Sheet(s) Filed in Color)

Pixels counted as signal data

Pixels counted as background data

Pixels counted as signal data of adjoining spots

The outline in bold is a square allocated to one spot

FIG. 3

| | k=2 | k=3 | k=4 | k=20 |
|---|---|---|---|---|
| 1 | 1 2 | 1 2 3 | 1 2 3 4 | 1 2 3 · · · 20 |
| 2 | 4 3 | 6 5 4 | 8 7 6 5 | · · · 22 21 |
| 3 | 5 6 | 7 8 9 | 9 10 11 12 | |
| 4 | 8 7 | 12 11 10 | 16 15 14 13 | |
| 5 | 9 10 | 13 14 15 | 17 18 19 20 | · · · · · 100 |
| 6 | 12 11 | 18 17 16 | · · · · | |
| 7 | 13 14 | 19 20 · | · · · · | |
| 8 | 16 15 | · · · | · · · · | |
| 9 | 17 18 | · · · | | |
| 10 | 20 19 | · · · | | |
| 11 | · · | | | |
| 12 | · | | | |
| 13 | · | | | |
| 14 | | | | |
| 15 | | | | |
| 16 | | | | |
| 17 | | | | |
| 18 | | | | |
| 19 | | | | |
| 20 | | | | | yk11n121ch1_nama_txt c110014_melanoma_ch2b_txt

| EXP | NAME | TYPE | GENE | CH1I | CH1B | CH1D | CH2I | CH2B | CH2D | PLAT | PROW | PCOL |
|---|---|---|---|---|---|---|---|---|---|---|---|---|
| y1ln121 | GENOMIC 1X | CONTROL | | 74 | 6 | 68 | 19 | 6 | 13 | CONTROL | A | 1 |
| y1ln121 | GENOMIC 1X | CONTROL | | 58 | 6 | 52 | 18 | 5 | 13 | CONTROL | A | 2 |
| y1ln121 | GENOMIC 1X | CONTROL | | 90 | 7 | 83 | 33 | 5 | 28 | CONTROL | A | 3 |
| y1ln121 | GENOMIC 1X | CONTROL | | 65 | 5 | 60 | 16 | 5 | 11 | CONTROL | A | 4 |
| y1ln121 | 3XSSC | CONTROL | | 61 | 6 | 55 | 107 | 6 | 101 | CONTROL | A | 5 |
| y1ln121 | 3XSSC | CONTROL | | 41 | 5 | 36 | 43 | 5 | 38 | CONTROL | A | 6 |
| y1ln121 | 3XSSC | CONTROL | | 24 | 8 | 16 | 17 | 6 | 11 | CONTROL | A | 7 |
| y1ln121 | 3XSSC | CONTROL | | 49 | 5 | 44 | 33 | 4 | 29 | CONTROL | A | 8 |
| y1ln121 | GENOMIC 0.5X | CONTROL | | 109 | 5 | 104 | 82 | 6 | 76 | CONTROL | A | 9 |
| y1ln121 | GENOMIC 0.5X | CONTROL | | 86 | 5 | 81 | 73 | 5 | 68 | CONTROL | A | 10 |
| ... | ... | ... | ... | ... | ... | ... | ... | ... | ... | ... | ... | ... |
| y1ln121 | YKL083W | ORF | YKL083W | 15 | 5 | 10 | 12 | 5 | 7 | 10 | A | 1 |
| y1ln121 | YKL095W | ORF | YJU2 | 50 | 5 | 45 | 50 | 6 | 44 | 10 | A | 2 |
| y1ln121 | YKL084W | ORF | YKL084W | 93 | 5 | 88 | 49 | 5 | 44 | 10 | A | 3 |
| y1ln121 | YKL096W | ORF | CWP1 | 197 | 5 | 192 | 2072 | 5 | 2067 | 10 | A | 4 |
| y1ln121 | YKL085W | ORF | MDH1 | 179 | 5 | 174 | 1127 | 6 | 1121 | 10 | A | 5 |
| y1ln121 | YKL097C | ORF | YKL097C | 25 | 4 | 21 | 24 | 6 | 18 | 10 | A | 6 |
| y1ln121 | YKL086W | ORF | YKL086W | 70 | 5 | 65 | 49 | 5 | 44 | 10 | A | 7 |
| y1ln121 | YKL097W-A | ORF | CWP2 | 877 | 6 | 871 | 572 | 5 | 567 | 10 | A | 8 |
| y1ln121 | YKL087C | ORF | CYT2 | 86 | 5 | 81 | 124 | 6 | 118 | 10 | A | 9 |
| y1ln121 | YKL098W | ORF | YKL098W | 69 | 5 | 64 | 57 | 6 | 51 | 10 | A | 10 |
| ... | ... | ... | ... | ... | ... | ... | ... | ... | ... | ... | ... | ... |
| y1ln121 | YOR335C | ORF | ALA1 | 344 | 11 | 333 | 44 | 11 | 33 | 19 | H | 15 |
| y1ln121 | YOR359W | ORF | YOR359W | 48 | 10 | 38 | 27 | 8 | 19 | 19 | H | 16 |
| y1ln121 | YOR336W | ORF | KRE5 | 55 | 9 | 46 | 46 | 11 | 35 | 19 | H | 17 |
| y1ln121 | YOR360C | ORF | PDE2 | 114 | 11 | 103 | 108 | 12 | 96 | 19 | H | 18 |
| y1ln121 | YOR337W | ORF | TEA1 | 43 | 11 | 32 | 22 | 11 | 11 | 19 | H | 19 |
| y1ln121 | YOR361C | ORF | PRT1 | 691 | 10 | 681 | 112 | 8 | 104 | 19 | H | 20 |
| y1ln121 | YOR338W | ORF | YOR338W | 37 | 10 | 27 | 26 | 12 | 14 | 19 | H | 21 |
| y1ln121 | YOR363C | ORF | PIP2 | 34 | 10 | 24 | 42 | 10 | 32 | 19 | H | 22 |
| y1ln121 | YOR339C | ORF | YOR339C | 23 | 10 | 13 | 14 | 10 | 4 | 19 | H | 23 |
| y1ln121 | YOR370C | ORF | MRS6 | 282 | 10 | 272 | 169 | 8 | 161 | 19 | H | 24 |
| ... | ... | ... | ... | ... | ... | ... | ... | ... | ... | ... | ... | ... |

FIG. 12

METHOD FOR EVALUATING UNIFORMITY OF SPOTS ON AN ARRAY

FIELD OF THE INVENTION

The present invention relates to a method for evaluating the uniformity of spots printed on an array, and is a technique supporting the analysis of an array having spots located two-dimensionally on a substrate, such as a DNA microarray, a DNA chip, a protein array, etc.

BACKGROUND OF THE INVENTION

Research involving the analysis of gene information, as typified by the Human Genome Project, is occurring at an ever faster pace worldwide, bringing with it an increasing need for new methodologies capable of efficiently analyzing expressions at the in-vivo gene level.

A new method for measuring gene expression levels in cells is a DNA microarray, wherein several hundred to several tens of thousands of samples of DNA are aligned and fixed in spots in a matrix shape to a glass slide. mRNA (the target) that has been extracted and purified from target cells is hybridized on the DNA microarray.

Fundamentally, the common method for performing measurements using DNA microarrays is two-color fluorescence labeling. In this method, mRNA originating from two types of cells (for example, normal cells and cancer cells) is extracted and purified, and the cells are labeled with fluorescent materials (CY3 and CY5) that have mutually differing excitation wave lengths. Then, competitive hybridization is performed on the same spots on the DNA microarray, and the fluorescent intensity of each spot on the array is measured by using two channels (CH1 and CH2) to view the mutually differing excitation wave lengths CY3 and CY5. By this means, the comparative quantity of gene level expression of the two types of cells is measured. In practice, after the fluorescent signals have been measured, the measurement results are superposed and color analysis is performed.

The data from CY3 and CY5 is normally calculated based on the following relational expression, with essentially the value of log (R/G) being utilized as the gene expression data.

(Sample A CY3 fluorescence data)
CH1–CH1B (Channel 1 background)=data R of CY3 (red)

(Sample B CY5 fluorescence data)
CH2–CH2B (Channel 2 background)=data G of CY5 (green)

Here, CH1 (channel 1) and CH2 (channel 2) are the measured fluorescent intensity values of the spots (channel 1 and 2 existing so as to measure red and green separately), measured using a laser scanner. Further, CH1B (background data of channel 1) and CH2B (background data of channel 2) are background data of the spots measured using a laser scanner.

Gene spots with a greater degree of gene expression in Sample A show as red, spots with a greater degree of gene expression in Sample B show as green, and spots with an approximately equal degree of gene expression show as yellow. That is, the spots show the following colors, in accordance with the ratio of R to G:

R/G>1 Red
R/G=1 Yellow
R/G<1 Green

As research based on DNA microarray data, such as the analysis of periodicity between genes, gene expression networks, and gene transfer control cascades, is being developed, and mathematical informational methods of this second generation research crucially require improved accuracy. A high degree of reliability is required with respect to the data from DNA microarrays.

Further, highly accurate data is required in the case where cancer is diagnosed on the basis of gene expression data.

However, gene analysis using DNA microarrays has only recently begun, and there are many cases where the issue of reproducibility needs to be resolved.

In particular, it is known that printing, hybridization, processing of the slide surface, etc. readily causes changes in the shape and size of the spots, and that mechanical influences during the spotting process, such as the minute displacement, vibration, etc. of the printing pins or platform, readily cause changes in the position of the spots.

Although the uniformity of the spots on the DNA microarray is an important factor that affects the accuracy of signal data, a method for evaluating this uniformity does not exist.

The present invention presents an extremely simple method for evaluating the uniformity of the spots on an array such as a DNA microarray, etc.

DISCLOSURE OF THE INVENTION

Portions of the gene expression data from DNA microarrays have been made public for researchers to use. This gene expression data have been made public by Stanford University, MIT, and Harvard University. Stanford University have DNA microarray data base. In 1997, Professor Brown's group at Stanford University succeeded in analyzing, for the first time in the world, the total gene expression (6400 genes) of the yeast cell (this is also public data).

Inventors, who were concerned that there was some regularity in the gene expression quantities, obtained the total gene expression data of the yeast cell (TUP1) that was made public in the DNA microarray data base of Stanford University, rearranged the expression data in the chromosome order and gene order, and analyzed the gene expression data thus obtained.

The result was that, on multiplying by 2, the presence of weak periodicity was ascertained. However, these periods did not originate from the gene expression levels, but appeared due to the influence of background data.

The present inventors have discovered a relationship between the presence of periodicity in the background data (this background data being used as fluorescence intensity compensatory data) and the non-uniformity of spots, and have discovered that the presence of periodicity in the background data furthermore exerts an important influence on the analysis of gene expression data. The present invention has resulted from the further discovery by the inventors that this information can be applied not only to DNA microarrays, but also to all arrays having spots located two-dimensionally on a substrate, such as DNA chips, protein arrays, etc.

That is, the present invention is a method for evaluating a uniformity of spots on an array having a plurality of spots, these spots undergoing specific emissions as a result of the hybridization of target matter and tagged probe matter, wherein the uniformity of the spots is evaluated by examining whether patterns having periodicity are manifested in a sequence BG comprising background data obtained in a manner described below.

<Method for Preparing the Sequence BG>
(1) By applying an analysis software to images obtained by scanning the monochromatic emission of the array, background data for each spot are obtained.
(2) Concerning each spot, the corresponding plate No.(α) of the target matter and position (β, γ) are determined, wherein α is a symbol or a numerical symbol identifying the plate while β and γ respectively stand for the row and column of a matrix formed by plate holes.
(3) The No.(α) and the position (β, γ) on the plate are assigned to respective background data.
(4) The sequence BG consisting of the background data aligned in the orders of the plate NO.(α) (the first priority) and the position (β, γ) on the plate(the second priority) is obtained.

According to the present invention, the uniformity of spots on an array such as a DNA microarray or the like can be evaluated in an extremely simple manner.

According to the method of the present invention, the signal data obtained from an array such as a DNA microarray, or the like, can be analyzed with great accuracy by evaluating the uniformity of the spots on the array in advance.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3 shows an example of sequence $I_j$ (j=1, . . . , 100) displayed in a matrix group.

FIG. 12 shows an outline of the yeast cell DNA microarray data.

PREFERRED ASPECT TO EMBODY THE INVENTION

Figure 1:
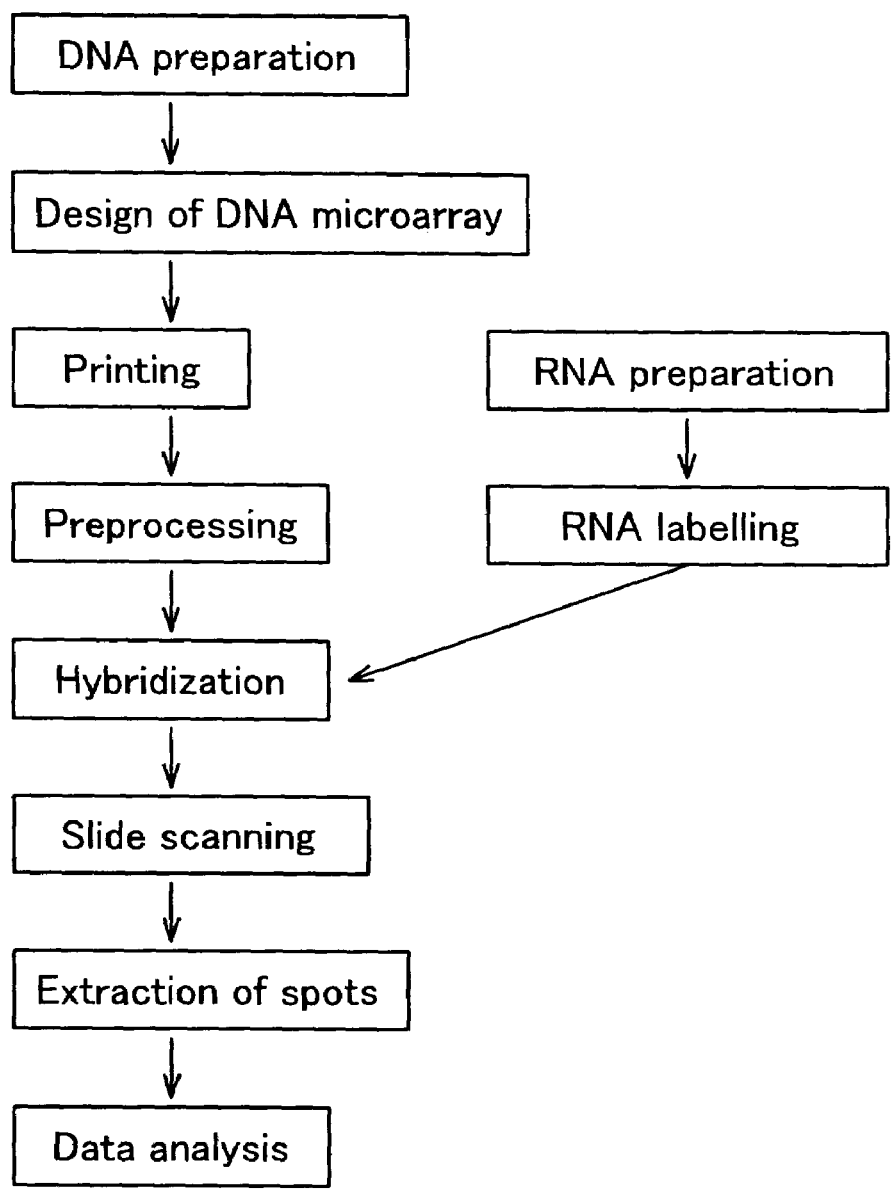
FIG. 1 shows a flow chart displaying the commonly used steps for analyzing signal data using a DNA microarray.

Below, a description is given using a DNA microarray as an example. A flow chart displaying the commonly used steps for analyzing signal data using a DNA microarray is as shown in FIG. 1.

Figure 2:
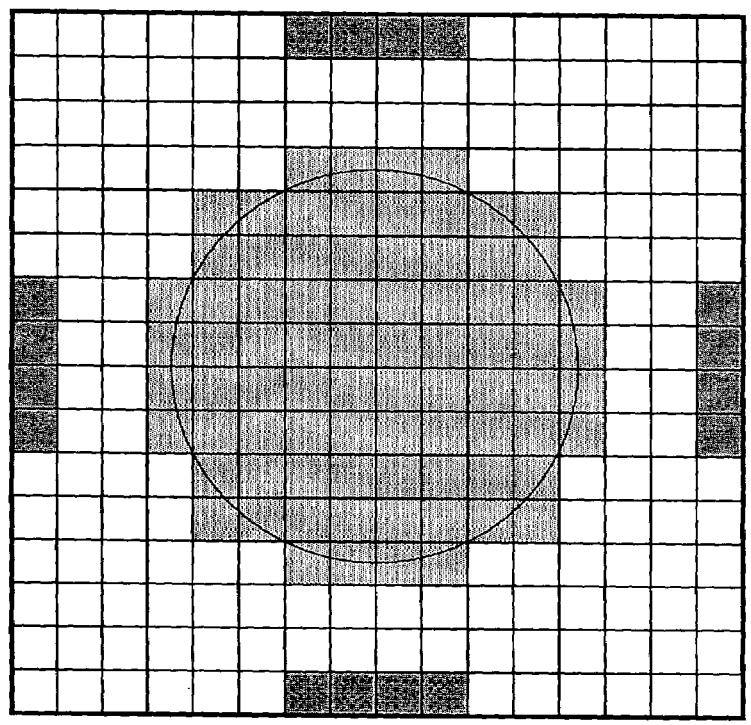
FIG. 2 shows a commonly seen distribution of one spot within an allocated square.
Figure 2:
Figure 2:
Figure 2:

<Background Data>
When scanning is performed on a slide on which hybridization has been completed, the color status of each spot on the slide is recorded as picture image data. Then, the picture image data is processed using analysis software, and color data of the spots is acquired. Specifically, the image obtained by scanning is overlaid with a grid image having a plurality of squares, one square being allocated for each spot, and then the signal data and background data within each square are acquired (FIG. 2).

Usually, the signal data is measured as the color intensity within an oval-shaped spot wherein a major axis and minor axis have been designated. The background data is measured as the intensity within the square surrounding the spot and in the area outside the boundaries of the spot.

The background data should be measured when all the spots are visible and emit at a brightness whereby the emission intensity is not saturated. There can be a slight variation in the background data depending on the detecting conditions of the emission signal of the scanning device or the method used by the analysis software for sampling the spots. However, the method of the present invention is not affected by the scanning device or the type of analysis software.

Preferred scanning devices are GenePix 4000A, GeneTACLSIV, GTMASS, GMS418Array Scanner, AvalancheMicroscanner, ChipReader, GeneTAC2000, CRBIO, ScanArray3000, 4000, 5000, etc.

Preferred analysis software is ScanAlyze, ArrayAnalyzer, ImaGene, AutoGene, QuantArray, QuantarrayAutomation, MicroArraySuite, ArrayVision, ArrayGauge, GenePixPro, etc.

<Method for Preparing Sequence BG>
In the present invention, a sequence BG serving as an indicator for revealing the characteristics of the background data is prepared as follows.
(1) By applying an analysis software to images obtained by scanning the monochromatic emission of the DNA microarray, background data for each spot are obtained.
(2) Concerning each spot, the corresponding plate No.(α) of the target DNA and position (β, γ) are determined, wherein α is a symbol or a numerical symbol identifying the plate while β and γ respectively stand for the row and column of a matrix formed by plate holes.
(3) The No.(α) and the position (β, γ) on the plate are assigned to respective background data.
(4) The sequence BG consisting of the background data aligned in the orders of the plate NO.(α) (the first priority) and the position (β, γ) on the plate(the second priority) is obtained.

<Display Methods for Patterns in the Sequence BG>
There is no particular restriction on the display methods of the present invention as long as these can be used to determine the presence in the sequence BG of patterns having periodicity.

Preferred display methods are the methods below.

(Display Method 1)

A method whereby a sub-sequence formed from 1 or more elements is extracted from a sequence, each number contained in the sub-sequence forming a color dot, wherein hue, luminosity, saturation, or a combination thereof, is defined by each type of number, the color dot further being sequentially output in a color dot matrix arranged in a matrix shape, a color pattern obtained from the output of the color dot matrix causing the intrinsic regularity to be revealed.

(Display Method 2)

A method whereby a sequence is divided into a plurality of sub-sequences, each number contained in the divided sub-sequences forming a sub-color dot column wherein hue, luminosity, saturation, or a combination thereof, is defined by each type of number, the sub-color dot columns being arranged in an aligned manner to output a color dot matrix wherein the color dots are arranged in a matrix shape, a color pattern obtained from the output of the color dot matrix causing latent characteristics within the sequence to be revealed.

A more preferred method is display method 3 below.

(Display Method 3)

A method whereby, in display method 1 or display method 2, each number forming a sequence $I_j$ (j=1, ..., m) is arranged according to the following positioning pattern:

$$(j = 1, 2, 3, \ldots, k)$$
$$(j = k+1, k+2, k+3, \ldots, k+k)$$
$$\vdots$$
$$(j = (n-1)k+1, (n-1)k+2, (n-1)k+3, \ldots, (n-1)k+k)$$
$$(j = nk+1, nk+2, nk+3, \ldots, nk+k)$$

(here, k is an integer of 2 or more, n is a natural number such that $nk+1 \leq m \leq nk+k$), a color dot matrix is output, latent characteristics within the sequence being revealed.

An even more preferred method is display method 4 below.

(Display Method 4)

A method whereby, when p is any given natural number less than m, and r is any given natural number, when the display method of display method 3 is implemented while substituting k=p, p+r, p+2r, p+3r, ..., a color dot matrix group is output wherein a color dot matrix of the p column, a color dot matrix of the p+r column, and color dot matrices of the p+2r, p+3r ... columns, as below, are all arranged in an aligned manner, latent characteristics within the sequence being revealed.

Display method 4 is particularly effective in the case where repeated units are totally unclear, or in the case where a portion of a sequence simply does not exist in repeated regions.

FIG. 3 schematically shows a method for arranging each element in sequence $I_j$ (j=1, ..., 100) obtained by means of method 4 as matrix groups consisting of the matrices k=1, k=2, k=3, k=4, ... and k=20.

<Method for Evaluating Uniformity of Spots>

When the sequence BG has been displayed by means of a suitable display method, it is verified whether patterns having periodicity are present. In the case where patterns having periodicity are present, it can be determined that the spots on the DNA microarray have low uniformity.

Various types of patterns having periodicity can be present in the sequence BG, such as a constantly repeated pattern or a plurality of types of patterns repeated across the entire sequence BG, patterns being repeated in portions of the sequence BG, etc.

If patterns having periodicity are not present in the sequence BG, it can be determined that the spots were printed uniformly, and consequently highly accurate data analysis is possible. On the other hand, if patterns having periodicity are present in even a portion of the sequence BG, the printing conditions of the spots were not uniform. Consequently the signal data has low reliability, and is influenced by compensatory factors, namely the patterns having periodicity of the background data. Since the periodic noise is included for signal data, the precise analysis is difficult.

Below, the method of the present invention is described more concretely.

<Embodiment 1>

(Yeast Cell DNA Microarray)

The yeast cell DNA microarray data from the DNA microarray data published by Stanford University was obtained (Genomic Expression Programs in the Response of Yeast Cells to Environmental Changes, Array Data File: y11n121 (variable heat 21C)).

An outline of the data that was obtained is shown in FIG. 12. In FIG. 12, 'CH1B' is background data of channel 1, and 'CH2B' is background data of channel 2. 'CH1D' and 'CH2D' are signal data of compensated spots obtained according to the following formula.

$$CH1\,I-CH1B=CH1D$$

$$CH2\,I-CH2B=CH2D$$

Further, in FIG. 12, 'PLAT' is a symbol or number identifying plates, 'PROW' is a symbol showing the rows of each plate, and 'PCOL' is a number showing the columns of each plate.

In FIG. 12, data concerning specific target DNA is displayed in row units. A plate number ('PLAT') and position on the plate ('PROW', 'PCOL') is assigned for the background data 'CH1B' and 'CH2B' for each item of target DNA displayed in the 'NAME' column. Each item of data is listed first in the plate number unit, then in the plate row unit, and finally in the plate column unit. Consequently, the order from top to bottom in FIG. 12 forms an order based on method 4 of the sequence BG of the present invention.

Figure 5:
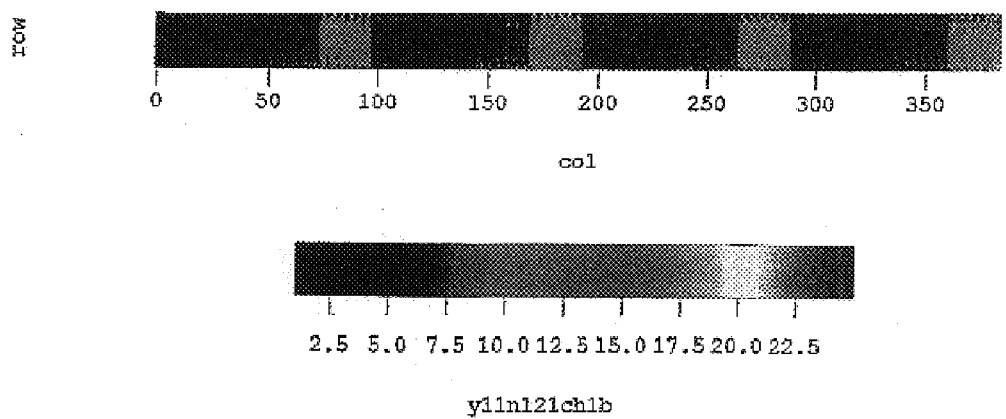
FIG. 5 shows an example of background data (CH1B) of the yeast cell DNA microarray data displayed as a colored matrix, the relationship between CH1B and the colors being shown in the lower row.

First, the background data (CH1B) is listed in sequence in the column 'CH1B' of FIG. 12 from the top line to the bottom line to form the sequence BG, this being displayed according to display method 4. Consequently, the presence of 384 repeat structures in the sequence BG is shown. This result is shown in FIG. 5, wherein each number in the sequence BG is displayed in a matrix shape according to display method 3 (here, k=384).

Figure 4:
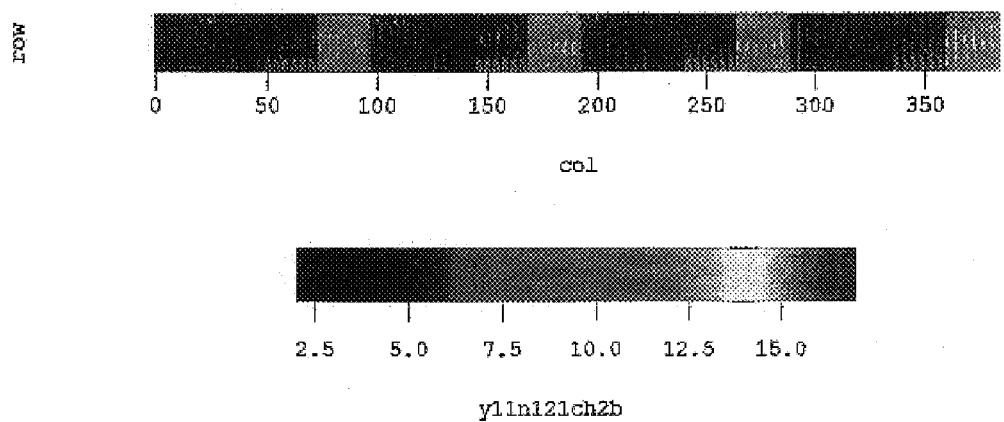
FIG. 4 shows an example of background data (CH2B) of yeast cell DNA microarray data displayed as a colored matrix, the relationship between CH2B and the colors being shown in the lower row.

Similarly, FIG. 4 shows the result wherein each number in the sequence BG of the background data (CH2B) is displayed in a matrix shape according to display method 3.

It can be seen from these figures that, in both the sequences BG of the background data CH1B and CH2B, periodically fluctuating patterns having distinct periodicity are present as 384 repeat units.

Figure 6:
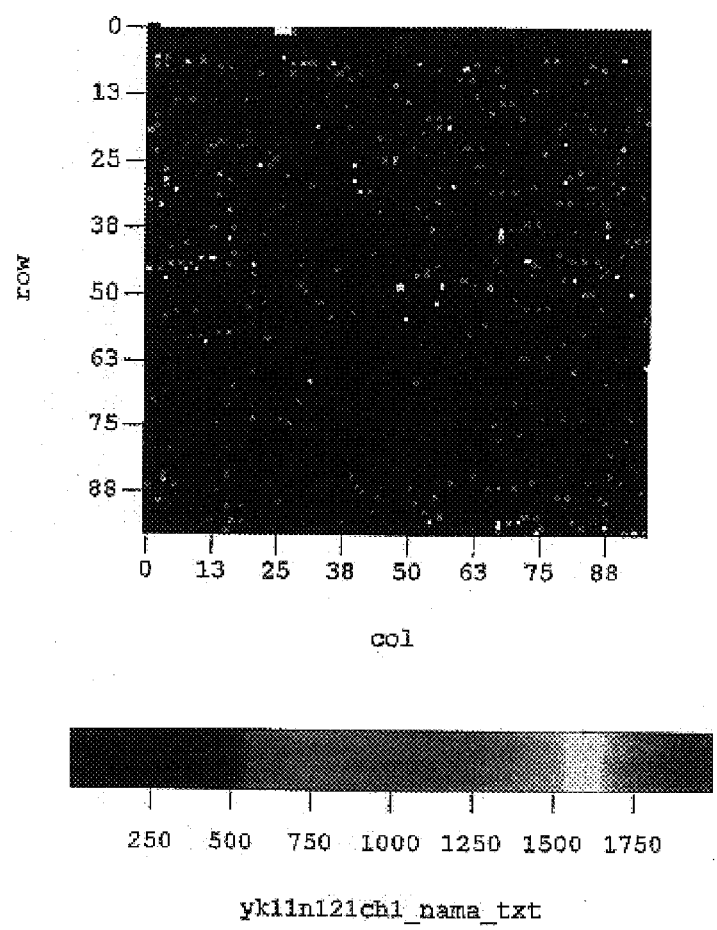
FIG. 6 shows signal data (CH1D) of channel 1 in a DNA microarray image wherein color is converted in accordance with the size of number values (Embodiment 1).
Figure 7:
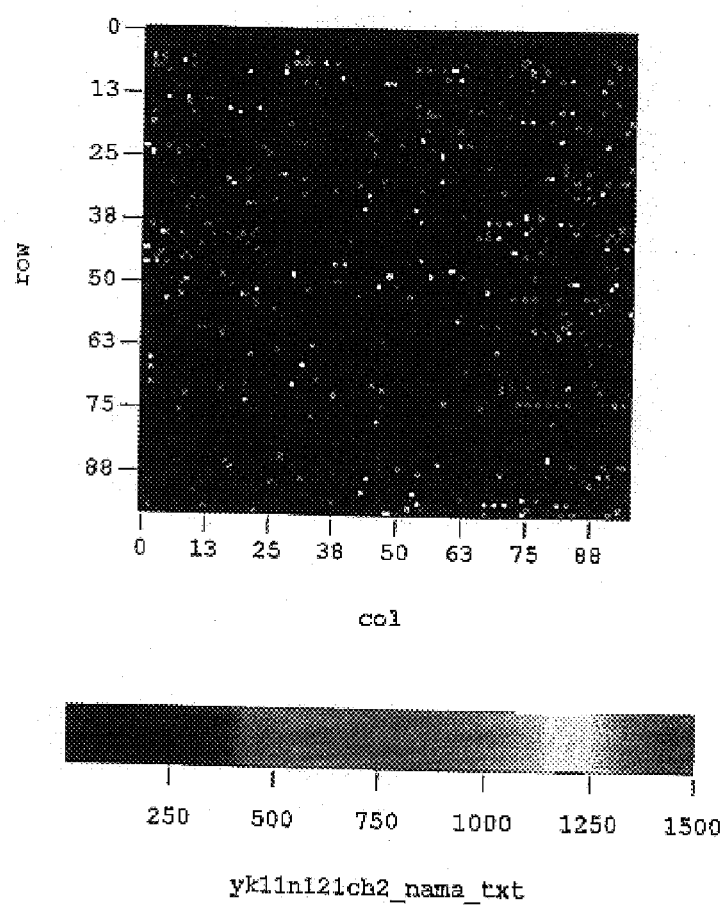
FIG. 7 shows signal data (CH2D) of channel 2 in a DNA microarray image wherein color is converted in accordance with the size of number values (Embodiment 1).

FIG. 6 shows the signal data 'CH1D' of channel 1 in a DNA microarray image wherein color is converted in accordance with the size of number values. Further, FIG. 7 shows a DNA microarray image of the signal data 'CH2D' of channel 2 processed in the same way. These DNA microarray images are not necessarily identical to actual scanned images, but schematically show the emission intensity of the spots in scanned images. The non-uniformity of the spots cannot be recognized at all from FIGS. 6 and 7, but since the distinct repeatability in the background data can be recognized from FIGS. 4 and 5, the non-uniformity of the spots can be determined.

Since the background data are utilized as compensatory number values of the fluorescent intensity, if there is periodicity in the background data itself, periodicity originating from the background data will necessarily be present in the gene expression data of the DNA microarray. Since this type of periodicity in the background data affects the reliability of the DNA microarray data, care is required during data analysis.

<Embodiment 2>

(Melanoma DNA Microarray)

The melanoma DNA microarray data from the DNA microarray data published by Stanford University was obtained (NC160 Cancer Microarray Project).

Figure 8:
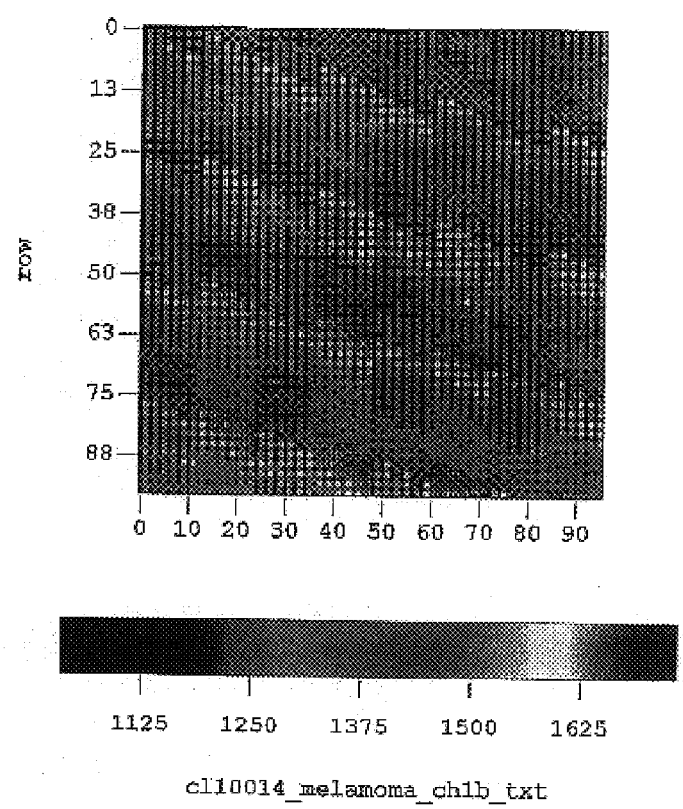
FIG. 8 shows an example of background data (CH1B) of melanoma DNA displayed as a colored matrix, the relationship between CH1B and the colors being shown in the lower row.

As with embodiment 1, background data (CH1B) is prepared, and is displayed according to display method 4. Consequently, the presence of 96 repeat structures in a sequence BG is shown (although it has also been suggested that 24 repeat structures are intrinsic to the sequence BG). FIG. 8 shows this result, wherein each number in the sequence BG is displayed in a matrix shape according to display method 3 (here, k=96).

Figure 9:
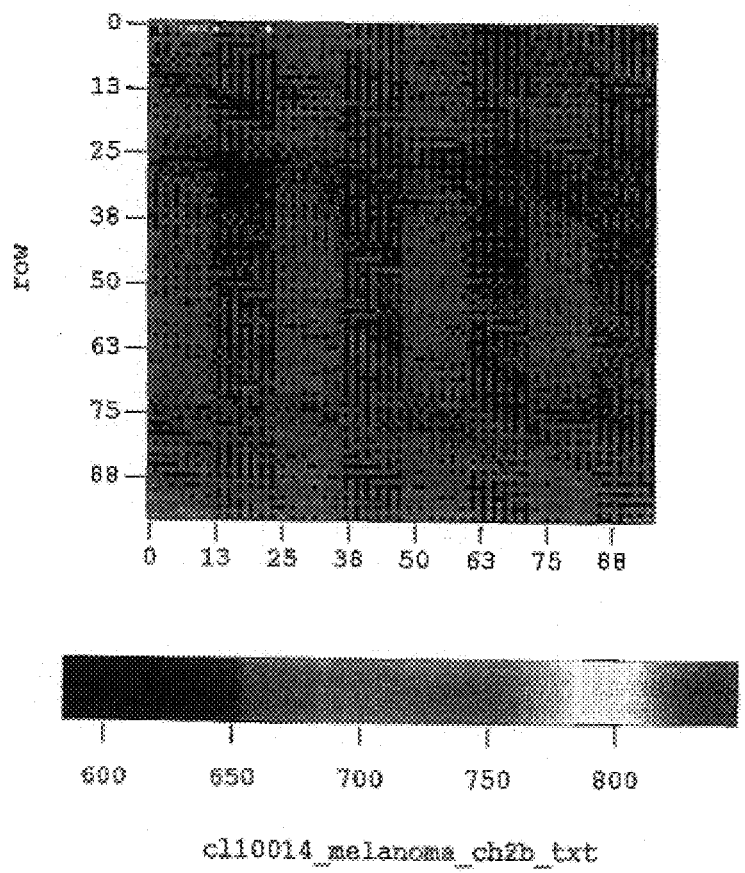
FIG. 9 shows an example of background data (CH2B) of the melanoma DNA displayed as a colored matrix, the relationship between CH2B and the colors being shown in the lower row.

Similarly, FIG. 9 shows this result, wherein each number in the sequence BG of the background data (CH2B) is displayed in a matrix shape according to display method 3.

In these figures, a plurality of vertical lines (that is, repeats of 96 units) are displayed distinctly, and it can be understood that patterns having periodicity are present in the sequences BG of the background data of CH1B and CH2B.

Figure 10:
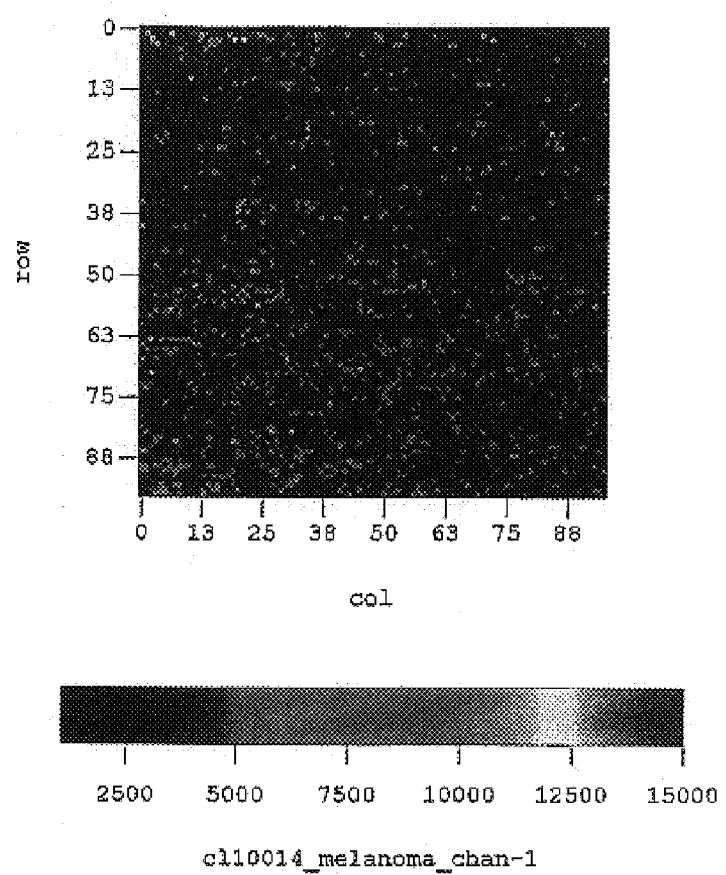
FIG. 10 shows signal data (CH1D) of channel 1 in a DNA microarray image wherein color is converted in accordance with the size of number values (Embodiment 2).
Figure 11:
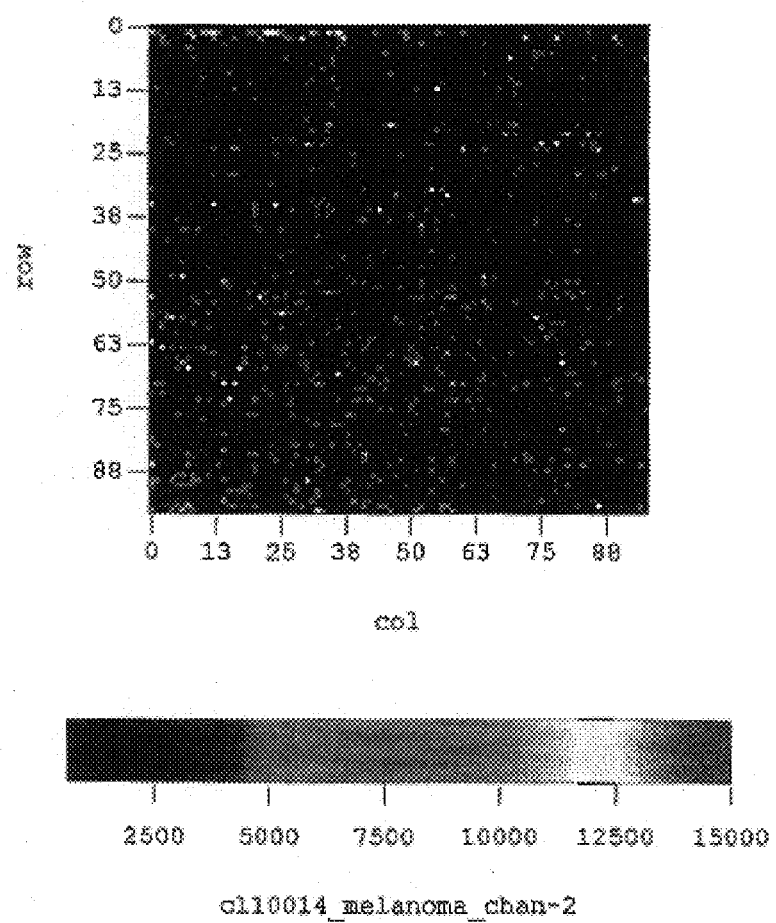
FIG. 11 shows signal data (CH2D) of channel 2 in a DNA microarray image wherein color is converted in accordance with the size of number values (Embodiment 2).

As with embodiment 1, the signal data 'CH1D' of channel 1 and the signal data 'CH2D' of channel 2 are shown in DNA microarray images in FIGS. 10 and 11. The non-uniformity of spots therein cannot be recognized at all from FIGS. 10 and 11, but since the distinct repeatability in the background data can be recognized from FIGS. 8 and 9, the non-uniformity of the spots can be determined.

According to the present invention, the uniformity of the spots on an array such as a DNA microarray or the like can be evaluated in an extremely simple manner.

According to the method of the present invention, by evaluating in advance the uniformity of the spots on the array, the signal data obtained from an array such as a DNA microarray or the like can be analyzed with great accuracy.

Specific examples of embodiments of the present invention are presented above, but these merely illustrate some possibilities of the invention and do not restrict the claims thereof. The art set forth in the claims includes transformations and modifications to the specific examples set forth above.

Furthermore, the technical elements disclosed in the present specification or figures may be utilized separately or in all types of conjunctions and are not limited to the conjunctions set forth in the claims at the time of submission of the application. Furthermore, the art disclosed in the present specification or figures may be utilized to simultaneously realize a plurality of aims or to realize one of these aims.

The invention claimed is:

1. A method for evaluating a uniformity of spots on an array having a plurality of spots, these spots undergoing specific emissions as a result of the hybridization of target matter and tagged probe matter, wherein the uniformity of the spots is evaluated by examining whether patterns having periodicity are manifested in a sequence BG comprising background data obtained, the method comprising:

(1) obtaining background data for each spot by applying an analysis software to images obtained by scanning the monochromatic emission of the array;

(2) for each spot, the corresponding plate No.($\alpha$) of the target matter and position ($\beta$, $\gamma$) are determined, wherein $\alpha$ is a symbol or a numerical symbol identifying the plate while $\beta$ and $\gamma$ respectively stand for the row and column of a matrix formed by plate holes;

(3) the No.($\alpha$) and the position ($\beta$, $\gamma$) on the plate are assigned to respective background data; and (4) the sequence BG consisting of the background data aligned in the orders of the plate No.($\alpha$) (the first priority) and the position ($\beta$, $\gamma$) on the plate (the second priority) is obtained.

2. A method as set forth in claim 1, the method being characterized in that the patterns in the sequence BG are displayed according to display method 1 or display method 2 described below, whereby it is determined whether the patterns having periodicity are manifested in the sequence BG, where display method 1 is a method whereby a sub-sequence formed from one or more elements is extracted from a sequence, the sub-sequence including a plurality of numbers, each number contained in the sub-sequence forming a color dot, wherein hue, luminosity, saturation, or a combination thereof, is defined by each type of number, the color dot further being sequentially output in a color dot matrix arranged in a matrix shape, a color pattern obtained from the output of the color dot matrix causing the intrinsic regularity to be revealed, and where display method 2 is a method whereby a sequence is divided into a plurality of sub-sequences, each sub-sequence including a plurality of numbers, each number contained in the divided sub-sequences forming a sub-color dot column wherein hue, luminosity, saturation, or a combination thereof, is defined by each type of number, the sub-color dot columns being arranged in an aligned manner to output a color dot matrix wherein the color dots are arranged in a matrix shape, a color pattern obtained from the output of the color dot matrix causing latent characteristics within the sequence to be revealed.

3. A method as set forth in claim 2, the method being characterized in that, in display method 1 or display method 2, each number forming a sequence $I_j$ ($j=1, \ldots, m$) is arranged according to the following positioning pattern:

$$(j = 1, 2, 3, \ldots, k)$$

$$(j = k+1, k+2, k+3, \ldots, k+k)$$

$$\vdots$$

$$(j = (n-1)k+1, (n-1)k+2, (n-1)k+3, \ldots, (n-1)k+k)$$

$$(j = nk+1, nk+2, nk+3, \ldots, nk+k)$$

(where, k is an integer of 2 or more, and n is a natural number such that $nk+1 \leq m \leq nk+k$), a color dot matrix is output, latent characteristics within the sequence being revealed.

4. A method as set forth in claim 3, the method being characterized in that when p is any given natural number less than m, and r is any given natural number, when the display method set forth above is implemented while substituting k=p, p+r, p+2r, p+3r, . . . , a color dot matrix group is output wherein color dot matrices of p, p+r, p+2r, p+3r . . . are all arranged in an aligned manner.

5. A method for evaluating a uniformity of spots on a DNA microarray having a plurality of spots, these spots undergoing specific emissions as a result of the hybridization of target DNA and tagged probe DNA, wherein the uniformity of the spots is evaluated by examining whether patterns having periodicity are manifested in a sequence BG comprising background data obtained, the method comprising:

(1) obtaining background data for each spot by applying an analysis software to images obtained by scanning the monochromatic emission of the DNA microarray;

(2) for each spot, the corresponding plate No.($\alpha$) of the target DNA and position ($\beta$, $\gamma$) are determined, wherein a is a symbol or a numerical symbol identifying the plate while $\beta$ and $\gamma$ respectively stand for the row and column of a matrix formed by plate holes;

(3) the No.($\alpha$) and the position ($\beta$, $\gamma$) on the plate are assigned to respective background data;

(4) the sequence BG consisting of the background data aligned in the orders of the plate No.($\alpha$) (the first priority) and the position ($\beta$, $\gamma$) on the plate (the second priority) is obtained.

6. A method as set forth in claim 5, the method being characterized in that the patterns in the sequence BG are displayed according to display method 1 or display method 2 described below, whereby it is determined whether the patterns having periodicity are manifested in the sequence BG, where display method 1 is a method whereby a sub-sequence formed from one or more elements is extracted from a sequence, the sub-sequence including a plurality of numbers, each number contained in the sub-sequence forming a color dot, wherein hue, luminosity, saturation, or a combination thereof, is defined by each type of number, the color dot further being sequentially output in a color dot matrix arranged in a matrix shape, a color pattern obtained from the output of the color dot matrix causing the intrinsic regularity to be revealed and where display method 2 is a method whereby a sequence is divided into a plurality of sub-sequences, each of the sub-sequences including a plurality of numbers, each number contained in the divided sub-sequences forming a sub-color dot column wherein hue, luminosity, saturation, or a combination thereof, is defined by each type of number, the sub-color dot columns being arranged in an aligned manner to output a color dot matrix wherein the color dots are arranged in a matrix shape, a color pattern obtained from the output of the color dot matrix causing latent characteristics within the sequence to be revealed.

* * * * *

UNITED STATES PATENT AND TRADEMARK OFFICE
CERTIFICATE OF CORRECTION

| | | |
|---|---|---|
| PATENT NO. | : 7,186,510 B2 | Page 1 of 1 |
| APPLICATION NO. | : 10/485030 | |
| DATED | : March 6, 2007 | |
| INVENTOR(S) | : Tetsuhiko Yoshida | |

It is certified that error appears in the above-identified patent and that said Letters Patent is hereby corrected as shown below:

ON THE TITLE PAGE:

Item (75) Inventor:

Please correct the Inventor's name to read Tetsuhiko Yoshida.

Signed and Sealed this

Fifth Day of June, 2007

JON W. DUDAS
*Director of the United States Patent and Trademark Office*